United States Patent
Weinheimer et al.

[19]

[11] Patent Number: 6,089,541
[45] Date of Patent: Jul. 18, 2000

[54] VALVE HAVING A VALVE BODY AND A DEFORMABLE STEM THEREIN

[75] Inventors: Jacek M. Weinheimer, Treasure Island; Edward Welling, Seminole, both of Fla.

[73] Assignee: Halkey-Roberts Corporation, St. Petersburg, Fla.

[21] Appl. No.: 09/151,378

[22] Filed: Sep. 10, 1998

Related U.S. Application Data

[60] Provisional application No. 60/059,323, Sep. 17, 1997.

[51] Int. Cl.[7] .......................... A61M 39/26; F16K 51/00
[52] U.S. Cl. .................................. 251/149.6; 251/149.4; 251/149.1; 604/33; 604/905
[58] Field of Search ........................ 251/149.1, 149.4, 251/149.6; 222/501; 604/33, 83, 246, 249, 905

[56] References Cited

U.S. PATENT DOCUMENTS

| | | |
|---|---|---|
| 3,806,086 | 4/1974 | Cloyd . |
| 4,917,668 | 4/1990 | Haindl . |
| 5,080,654 | 1/1992 | Picha et al. . |
| 5,108,380 | 4/1992 | Herlitze et al. . |
| 5,242,393 | 9/1993 | Brimhall et al. . |
| 5,330,435 | 7/1994 | Vaillancourt . |
| 5,349,984 | 9/1994 | Weinheimer et al. . |
| 5,360,413 | 11/1994 | Leason et al. . |
| 5,380,306 | 1/1995 | Brinon . |
| 5,474,536 | 12/1995 | Bonaldo . |
| 5,474,544 | 12/1995 | Lynn . |
| 5,501,426 | 3/1996 | Atkinson et al. ............... 251/149.1 |
| 5,509,433 | 4/1996 | Paradis . |
| 5,509,912 | 4/1996 | Vaillancourt et al. . |
| 5,520,666 | 5/1996 | Choudhury et al. . |
| 5,533,708 | 7/1996 | Atkinson et al. . |
| 5,549,566 | 8/1996 | Elias et al. . |
| 5,616,130 | 4/1997 | Mayer . |
| 5,699,821 | 12/1997 | Paradis ............................ 251/149.1 |
| 5,820,601 | 10/1998 | Mayer ............................. 251/149.1 |

OTHER PUBLICATIONS

Safe Connect, Winfield Medical, 10 page brochure.
Quality Check Valves from Burron, Burron Medical Inc., one page brochure.
SoloPak Maxcess Needleless System, SoloPak Pharmaceuticals, Inc., two page brochure.
The MMG MLI–Set, MMG Infusion Technologies, one page brochure.
Clave Connector, Clave1, Rev. Mar. 1994, two page brochure.
Smart Site Needleless System, Alaris Medical Systems Inc., two page brochure, May 1997.

*Primary Examiner*—Kevin Shaver
*Assistant Examiner*—Eric Keasel
*Attorney, Agent, or Firm*—Trexler, Bushnell, Giangiorgi & Blackstone, Ltd.

[57] ABSTRACT

Disclosed is a valve engageable with an instrument, where the valve includes a deformable stem located in a valve body and shiftable from a first position. When an instrument is engaged with an aperture in the stem, the stem is urged from the first position into the valve body and the aperture deforms to allow liquid to flow through the stem, to or from the instrument. The stem and the valve body are configured such that when the instrument is not engaged with the stem, the valve body engages the stem and urges the aperture closed.

22 Claims, 5 Drawing Sheets

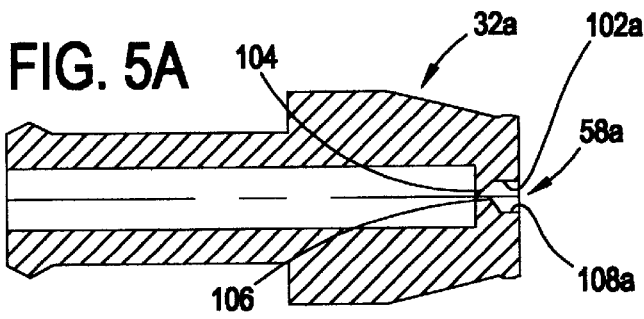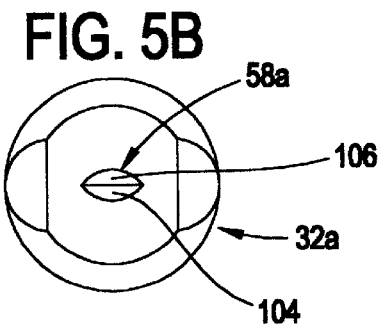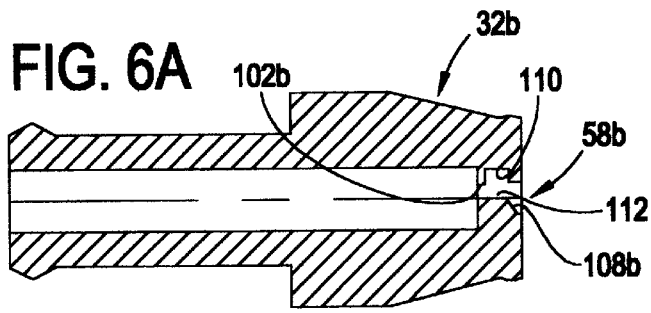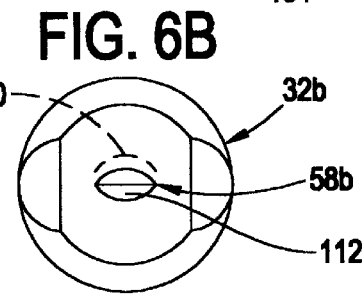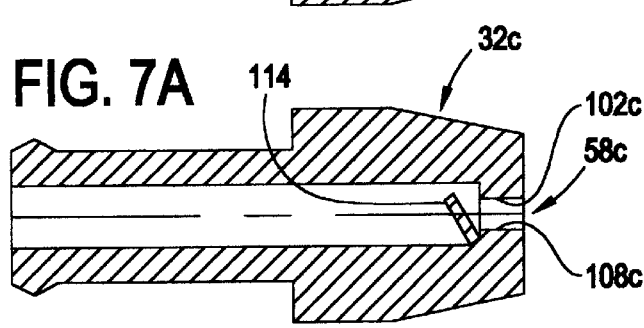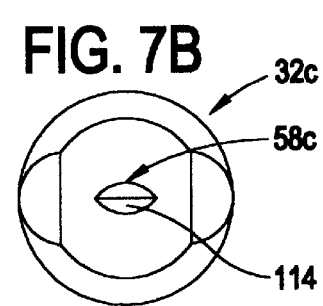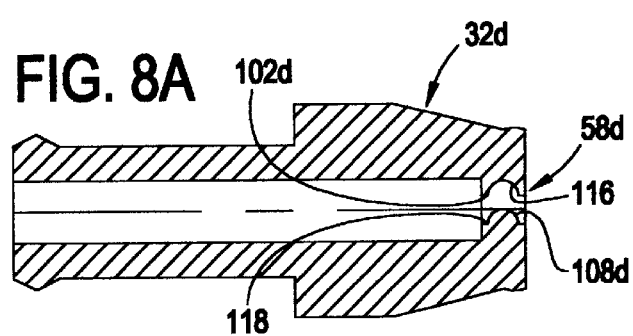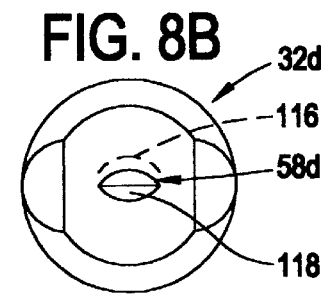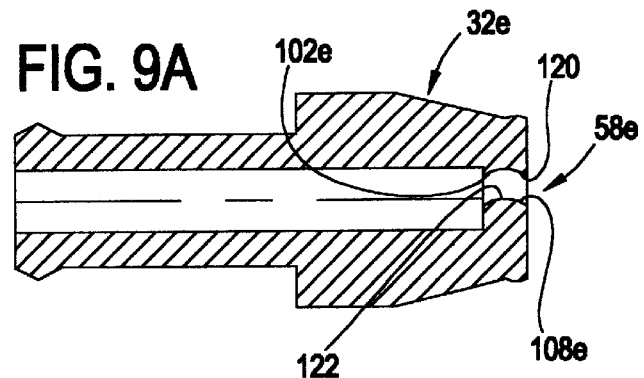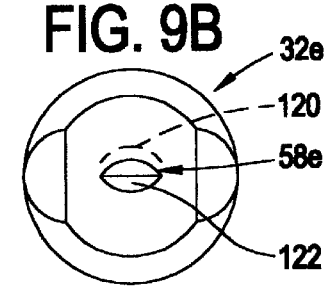

VALVE HAVING A VALVE BODY AND A DEFORMABLE STEM THEREIN

RELATED APPLICATIONS

This application claims the benefit of U.S. Provisional Application Ser. No. 60/059,323, filed Sep. 17, 1997.

BACKGROUND

The present invention relates generally to valves, and relates more specifically to a novel valve construction that provides many improved features over the prior art, and is well adapted for medical usage, such as in needleless IV sets, and other medical applications where it is desirable to avoid use of needles in the transmission and delivery of fluid products in a sterile environment.

Presently, there are many types of valves such as check valves which are designed to control the one-way flow of a fluid therethrough. One common type of check valve comprises a valve element, such as a ball or a spring biased valve stem, reciprocatingly positioned within a valve body providing a fluid passageway. The flow of fluid in one direction through the valve body is permitted upon displacement of the stem as it flows around the valve element to exit the valve body. However, in the opposite direction, the flow of fluid along with the spring forces the valve element against a valve seat, thereby inhibiting, or checking, the flow of fluid therethrough. In this manner, this type of check valve effectively provides that fluid can flow only in one direction through the check valve. An example of this type of valve can be found in U.S. Pat. No. 5,349,984.

Instead of necessitating fluid flow in an opposite direction in order to provide that the valve element is forced into the valve seat, some check valves provide means associated with the valve element for constantly urging the valve element into the valve seat. For example, a compression spring is often disposed within the valve body for this purpose. Because of the constant urging of the valve element into the valve seat by the compression spring, some amount of pressure must be exerted on the valve element to unseat same from the valve seat and allow fluid to flow therepast.

The check valves described above provide several disadvantages. For example, while the seating of the valve element in the valve seat provides that fluid cannot flow therepast, this does not provide that the end of the check valve body is sealed. As a result, bacteria or other contaminants may enter the valve body and accumulate in the valve body between the end of the valve body and the seated valve element. Additionally, often the valve element is disposed in the valve body some distance from the end of the valve body, therefore it may prove difficult to adequately clean or sterilize the check valve. In many applications, it is important to provide that the check valve is kept clean and sterile, such as in medical applications when, for example, fluid is being injected therethrough into a patient.

Moreover, in the case where a check valve is provided with a compression spring for urging the valve element into the valve seat, the fluid traveling through the check valve contacts the compression spring. In fact, fluid or other material on the other side of the check valve can contact the compression spring even when the valve element is seated in the valve seat. As a result, certain material can build up on the compression spring. For example, corrosion can build up on the compression spring over time, some metallic components can leach into the fluid, or, within a medical application, bacteria can build up on the compression spring. Because incoming fluid contacts the compression spring as the fluid flows through the check valve, the material which has built up on the compression spring may join the incoming fluid and flow out the check valve along with the incoming fluid. This is undesirable in most situations, and is especially undesirable within medical applications where sterility is a priority. Check valves in the medical field often provide even more areas at which bacteria can collect.

Furthermore, in medical applications, it is usually desirable to restrict exposure to the fluid being injected or extracted from the patient, and insulate nurses and doctors from exposure to said liquid. However, often the instrument used to inject or withdraw the fluid retains some of the fluid on the tip thereof, thus providing a risk to nurses and doctors of being exposed to the fluid.

The present invention is directed to address the problems encountered heretofore which are discussed hereinabove.

OBJECTS AND SUMMARY OF THE DISCLOSURE

A general object of the present invention is to provide a valve which seals itself to restrict fluid flow thereinto, and decreases the risk of contaminants such as bacteria collecting on or within the valve. All external surfaces in the proximity of a stem are accessible to be wiped clean with a sterile swab.

Another object of the present invention is to provide a valve which restricts fluid flow therethrough without requiring fluid pressure in the opposite direction and which does so without providing a compression spring that is exposed to fluid or liquid being handled by the valve.

Still another object of the present invention is to provide a valve which seals with an instrument when the instrument is engaged therewith so that there is no leakage of fluid.

Yet another object of the present invention is to provide a valve which automatically wipes an instrument clean upon the instrument being disengaged therefrom.

Yet still another object of the present invention is to provide a valve which allows fluid flow in both directions upon an instrument being engaged therewith.

Briefly, and in accordance with the above, the present invention envisions a valve engageable with an instrument, where the valve includes a deformable stem located in a valve body and shiftable from a first position. When an instrument is engaged with an aperture in the stem, the stem is urged from the first position into the valve body and the aperture deforms to allow liquid to flow through the stem, to or from the instrument. The stem and the valve body are configured such that when the instrument is not engaged with the stem, the valve body engages the stem and urges the aperture closed.

BRIEF DESCRIPTION OF THE DRAWINGS

The organization and manner of the structure and function of the invention, together with further objects and advantages thereof, may be understood by reference to the following description taken in connection with the accompanying drawings, wherein like reference numerals identify like elements, and in which.

Figure 1A:
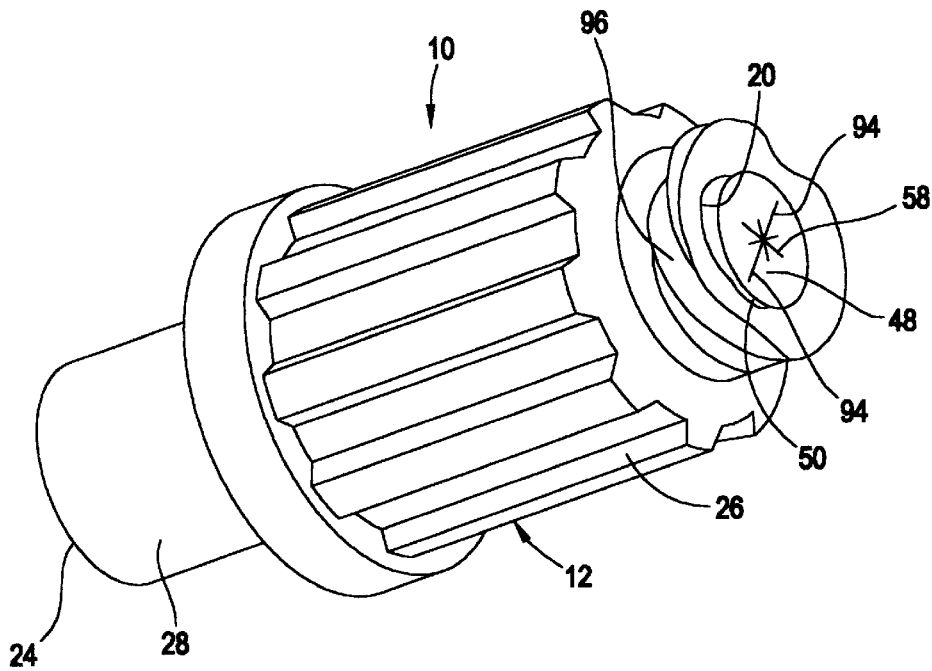
FIG. 1A is an enlarged isometric view of a valve in accordance with the present invention.
Figure 1B:
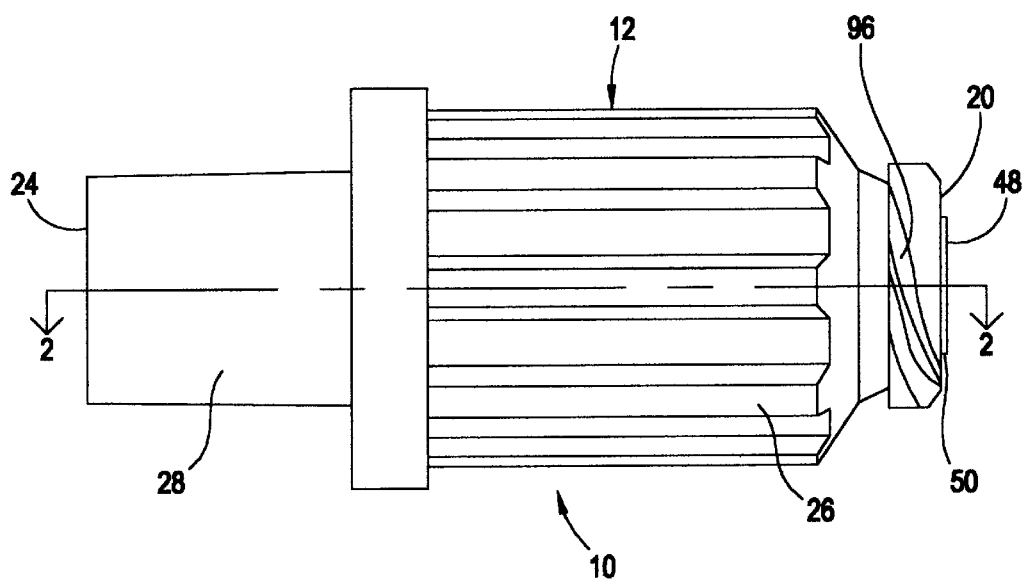
FIG. 1B is an enlarged, side elevational view of the valve shown in FIG. 1A.
Figure 2A:
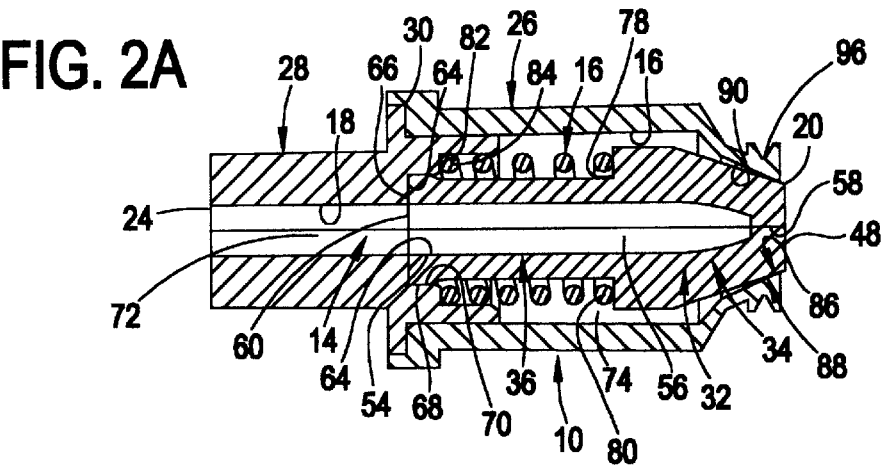
FIG. 2A is an enlarged, cross-sectional view, taken along line 2—2 of FIG. 1B, of the valve shown in FIGS. 1A and 1B.
Figure 2B:
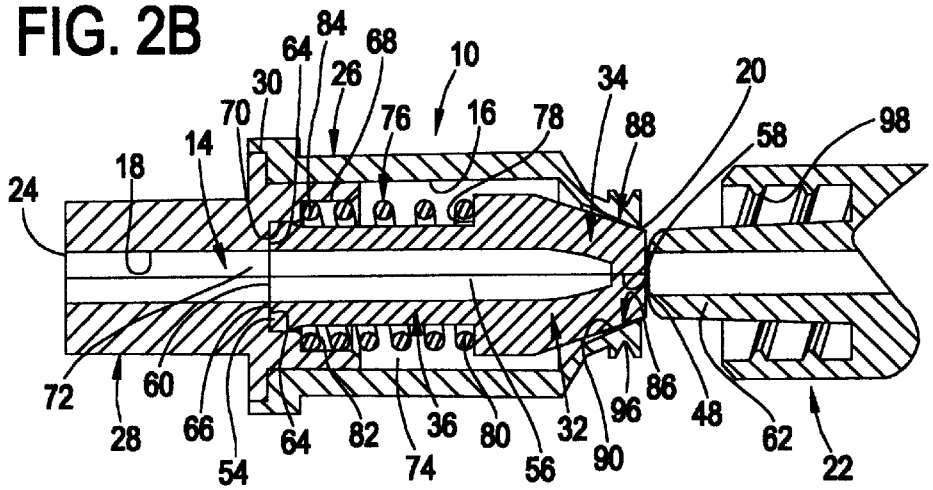
FIG. 2B is an enlarged, cross-sectional view, much like FIG. 2A, of the valve of FIGS. 1A and 1B showing a tip of an instrument beginning to be engaged therewith.
Figure 2C:
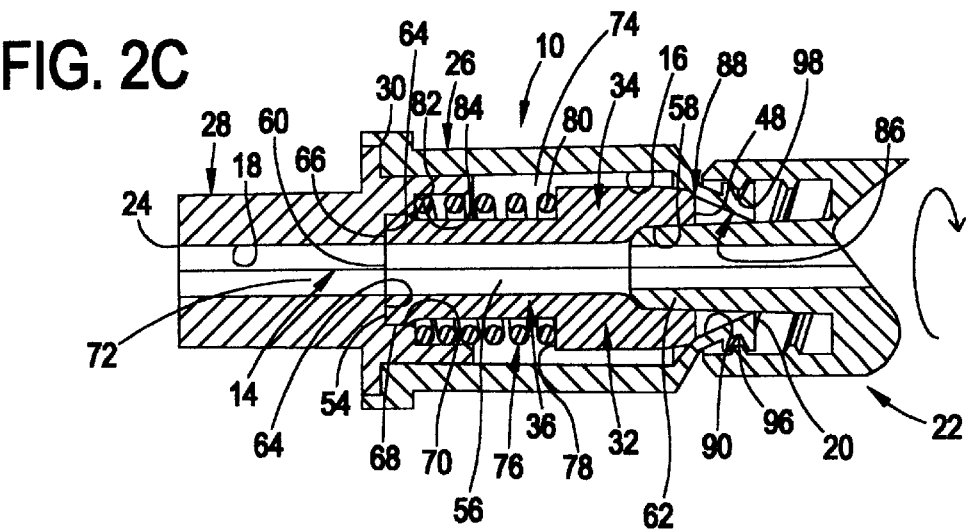
FIG. 2C is an enlarged, cross-sectional view, much like FIG. 2A, of the valve of FIGS. 1A and 1B showing the instrument fully engaged therewith and showing the tip of the instrument fully received by an aperture in a stem of the valve.
Figure 3A:
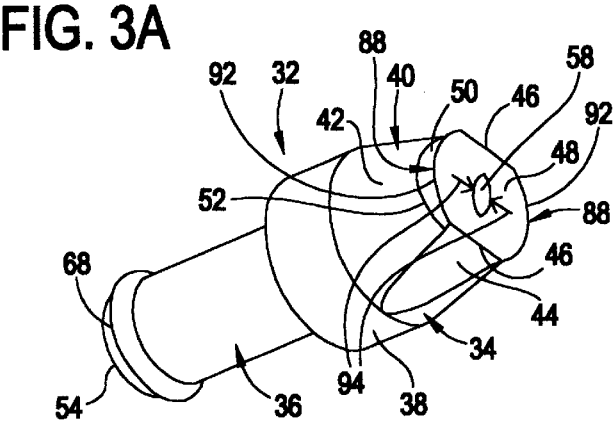
FIG. 3A is an enlarged isometric view of a stem of the valve shown in FIGS. 1A–1B and 2A–2C.
Figure 3B:
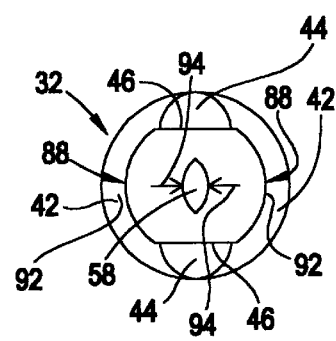
FIG. 3B is an enlarged, front elevational view of the stem shown in FIG. 3A.
Figure 3C:
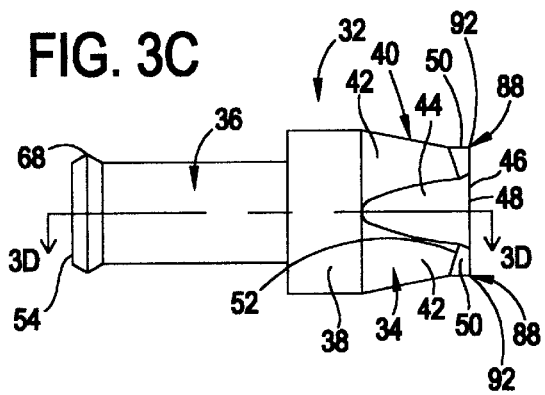
FIG. 3C is an enlarged, side elevational view of the stem shown in FIG. 3A.
Figure 3D:
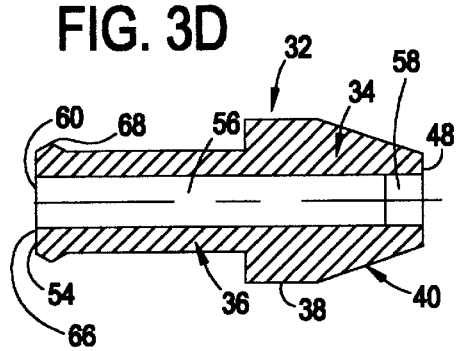
FIG. 3D is an enlarged cross-sectional view, taken along line 3D—3D of FIG. 3C, of the stem shown in FIG. 3C.
Figure 3E:
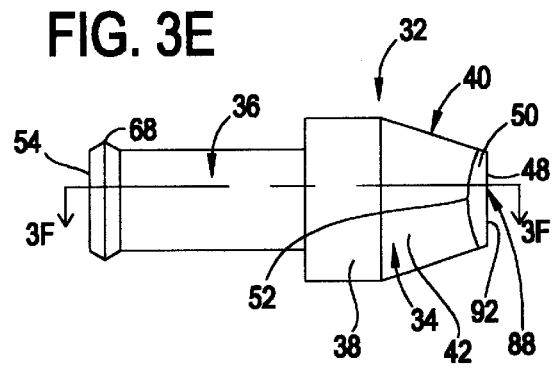
FIG. 3E is an enlarged, top plan view of the stem shown in FIG. 3A.
Figure 3F:
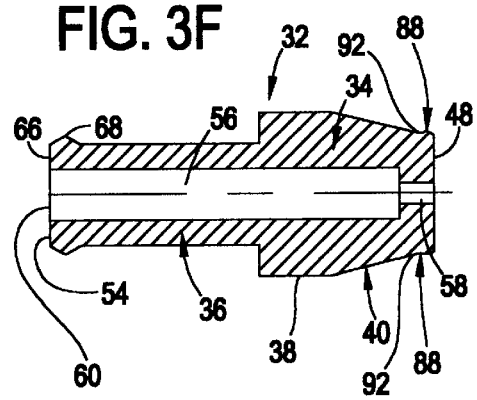
FIG. 3F is an enlarged cross-sectional view, taken along line 3F—3F of FIG. 3E, of the stem shown in FIG. 3E.
Figure 4A:
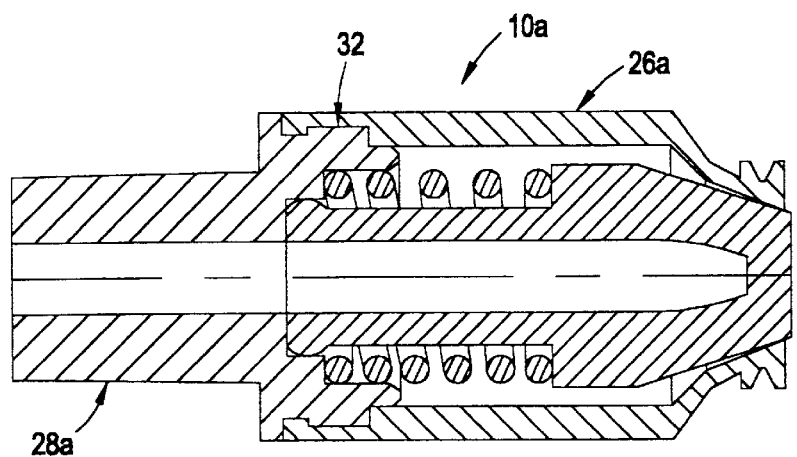
FIGS. 4A is an enlarged, cross-sectional view of a valve much like the valve shown in FIG. 2A, but showing an alternative snap joint between a body portion and an end portion thereof.
Figure 4B:
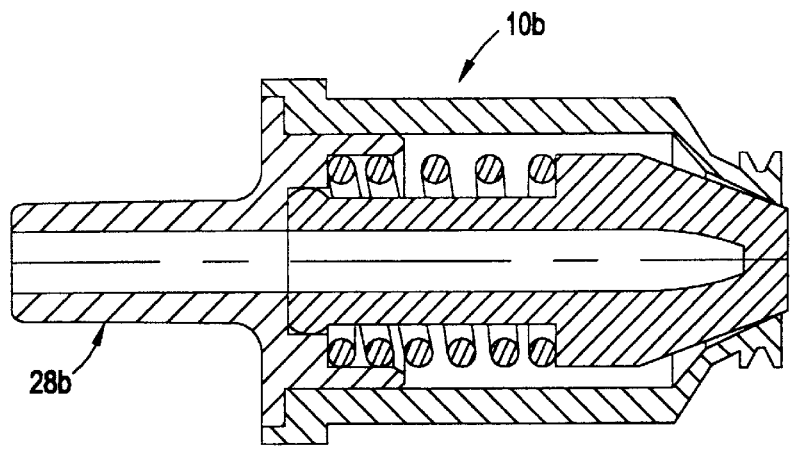
Figure 4C:
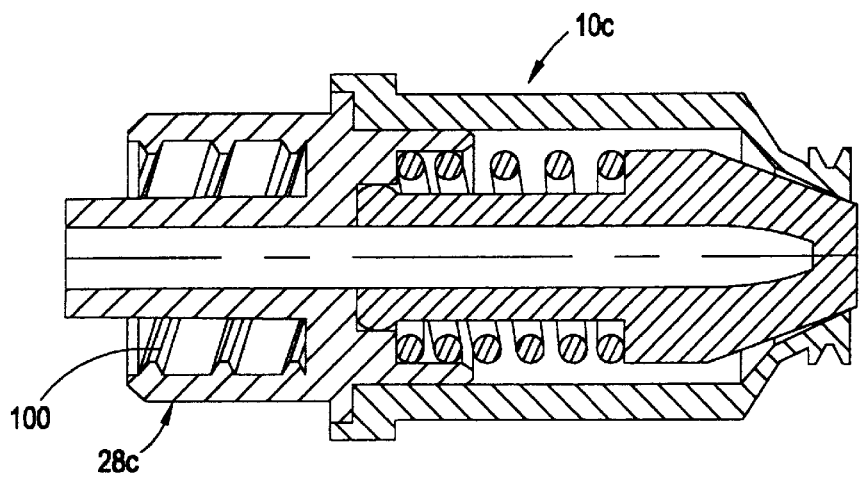

Each of FIGS. 4B and 4C is an enlarged, cross-sectional view, similar to the view of FIG. 2A, of a valve much like the valve shown in FIGS. 1A, 1B and 2A–2C, but showing an alternative end portion thereof, Each of FIGS. 5A, 6A, 7A, 8A and 9A is an enlarged cross-sectional view, similar to the view of FIG. 3F, each showing a different aperture of a stem which may be utilized in accordance with the present invention; and Each of FIGS. 5B, 6B, 7B, 8B and 9B is an enlarged front, elevational view of each of the stems shown in FIGS. 5A, 6A, 7A, 8A and 9A, respectively.

DESCRIPTION

Shown in the drawings are valve constructions, and portions thereof, in accordance with the present invention. Each of the valves shown seals to restrict fluid flow therethrough, and does so without requiring fluid flow in the opposite direction. Also, each of the valve constructions provides a seal with a tip of an instrument when the tip is engaged therewith and automatically wipes the tip of the instrument clean upon the instrument being disengaged therefrom. All external surface in the proximity of a stem are accessible to be wiped clean with a sterile swab. Further, each of the valves shown allows fluid flow in both directions upon the tip of the instrument being engaged therewith, and does not expose an interior neutral area of the valve to the fluid flowing through the valve. Therefore, each of the valves shown is specifically directed towards alleviating many problems encountered in the prior art, and providing a sterile fluid path for the delivery to or withdraw of fluid from a patient.

The valve 10 shown in FIGS. 1A, 1B, and 2A–2C will first be described. The valve 10 includes a substantially tubular valve body 12 having, as shown in FIGS. 2A–2C, a central axial bore 14 forming an enlarged diameter section 16 and a reduced diameter section 18. The bore 14 defines a first open end 20 for receiving an instrument 22, such as a needleless syringe having a cannula tip, and a second open end 24 for communication with a fluid line (not shown). Preferably, the valve body 12 is comprised of a relatively rigid, durable material such as a hard thermoplastic material.

As shown most clearly in FIGS. 2A–2C, for ease of assembly, the valve body 12 may be formed of two portions, a female front body portion 26 and a male back end portion 28, which are ultrasonically sealed together at a weld joint 30 to provide the continuous valve body 12. Ultimately, it should be appreciated that the location of the joint 30 is not imperative, and that the valve body 12 need not even be formed of two separate pieces that are connected together, but may be formed of even more pieces or may be formed as a unitary, single-bodied piece.

Within the valve body 12 is a stem 32. The overall shape and configuration of the stem 32 can best be seen in FIGS. 3A–3F in which the stem 32 is shown separate from the remainder of the valve 10. Preferably the stem 32 is comprised of silicone, but the stem 32 may instead be formed of some other resilient elastomer material, such as natural rubber, a thermoplastic elastomer, or a thermoplastic rubber.

The stem 32 preferably has a head portion 34 and a stem throat portion 36. The head portion 34 of the stem 32 is preferably somewhat bulbous and is formed of an enlarged diameter cylindrical portion 38 and a conical portion 40. Preferably, the conical portion 40 has opposing conical surfaces 42 which are adjacent opposing arcuate surfaces 44. As shown, each of the arcuate surfaces 44 begins at a corresponding flat 46 on an end surface 48 of the stem 32, and, while certainly not imperative to the present invention, terminates at the enlarged diameter cylindrical portion 38. Additionally, each of the conical surfaces 42 begins at a corresponding reduced diameter cylindrical portion 50 and terminates at the enlarged diameter cylindrical portion 38. As shown in FIGS. 3A, 3C and 3E, the intersection 52 between each conical surface 42 and corresponding reduced diameter cylindrical portion 50 is preferably arcuate, and each of the reduced diameter cylindrical portions 50 terminates at the end surface 48 of the stem 32. The stem throat portion 36 of the stem 32 is preferably substantially cylindrical to provide strong axial compression resistance, and terminates at an end 54 of the stem 32 opposite the end surface 48. The reduced diameter cylindrical portion 50 assists in closing the aperture 58 in the state depicted in FIG. 2A, but the same may be accomplished without including the reduced diameter cylindrical portion 50, but solely by the conical surfaces 42 and flats 44 terminating at the end surfaces 48.

As shown in FIGS. 3D and 3F, the stem 32 has a central axial fluid passageway 56 therethrough which defines, at one end of the passageway 56, an aperture 58 in the end surface 48 of the stem 32 and, at the other end of the passageway, defines an opposite, second end opening 60. While the second end opening 60 of the stem 32 is always open, the aperture 58 in the head portion 34 of the stem 32 is initially closed forming an internal hermetic seal as shown in FIGS. 2A and 2B. However, as shown in the progression from FIG. 2B to FIG. 2C, the aperture 58 can be opened by engaging a tip 62 of an instrument 22 therewith, such as the tip of a needleless syringe as will be described more fully later herein.

As shown in FIGS. 2A–2C, the end 54 of the throat portion 36 defines the second end opening 60 of the stem 32, and this end 54 is seated against a shoulder 64 within the valve body 12, thereby forming a sealed contact therebetween. To provide for an exceptional sealed contact, the end 54 of the throat portion 36 is provided with both a flat end portion 66 and an adjacent, outward protruding lip 68. While the flat end portion 66 of the stem 32 seals against the shoulder 64 within the valve body 12, the lip 68 seals against an adjacent internal side wall 70 within the valve body 12 thereby providing essentially two contact surfaces between the end 54 of the stem 32 and the valve body 12. One having ordinary skill in the art may recognize other ways in which to provide an exceptional sealed contact between the stem 32 and the valve body 12. As shown, preferably the second end opening in the stem 32 aligns with the reduced diameter section 18 within the valve body 12 thus providing a smooth fluid flow area 72 between the fluid passageway 56 in the stem 32 and the reduced diameter portion 18 of the valve body 12 for carrying a liquid, air or other fluid within the valve 10. Providing sealed contact between the end 54 of the stem 32 and the valve body 12 is important in order to prevent fluid from leaking into the neutral space 74 between the stem 32 and the valve body 12 from the fluid flow area 72. Leaking of fluid into the neutral space 74 can result in the leaking of fluid therefrom out the end 20 of the valve body 12 as well as provide other disadvantages which will be discussed more fully later herein.

The stem 32 is preferably configured such that it is urged toward the end 20 of the valve body 12. To this end, the stem 32 may be shaped such that it is naturally urged in into this position. Additionally, means may be provided for urging the end 48 of the stem 32 towards the end 20 of the valve body 12. Particularly, as shown in FIGS. 2A–2C, a compression spring 76 may be provided in the neutral space 74 between the stem 32 and the valve body 12. To this end, the stem 32 may be provided with an outwardly extending shoulder 78 at the base of the head portion 34 for engaging a first end 80 of the compression spring 76, and the valve body 12 may be provided with a shoulder 82 for engaging a second end 84 of the compression spring 76. In this manner, the compression spring 76 can compress between the stem 32 and the valve body 12 and urge the end 48 of the stem 32 towards the end 20 of the valve body 12. This compression is shown in FIG. 2C, and results from the tip 62 of the instrument 22 being inserted into the aperture 58 at the end 48 of the head portion 34 of the stem 32, as will be described more fully later herein. FIG. 2A shows the valve 10 when the tip 62 of the instrument 22 is not so engaged and FIG. 2B shows the valve 10 when the tip 62 of the instrument 22 is about to be engaged therewith. At either time, the compression spring 76 tends to restore itself to its free length, but can only reach the pre-loaded state, as shown. Should the compression spring 76 be provided, it becomes even more important to prevent fluid from leaking into the neutral space 74 between the stem 32 and the valve body 12 from the fluid flow area 72. Leaking of fluid into the neutral space 74 can cause the compression spring 76, if provided, to corrode or leach metallic components over time and subsequently the corrosion or leached metals can escape back into the fluid flow area 72 mixing with the flowing fluid. Or, within a medical application, leaking of fluid into the neutral space 74 can cause bacteria to collect on the compression spring 76, and subsequently the bacteria can escape back into the fluid flow area 72 mixing with the flowing fluid and exposing a patient thereto.

Instead of providing the compression spring 76 between the stem 32 and the valve body 12, the stem 32 may be configured such that it is naturally urged into position. For example, the stem throat 36 of the stem 32 may be provided as having a thick enough wall thickness and being robust enough to provide a sufficient spring rate in order to urge the end 48 of the stem 32 towards the first end 20 of the valve body 12. In this event, the stem 32 would be assembled in a compressed condition with the inherent resiliency of the material from which the stem 32 is constructed providing the necessary spring force. As such, the stem throat portion 36 may or may not include longitudinal ribs or the like to strengthen this section, yet provide resiliency, as shown in U.S. Pat. No. 5,349,984, which is incorporated herein by reference. Of course, even should the compression spring 76 not be included, it remains desirable to prevent the leaking of fluid into the neutral space 74 and the present invention provides as such. One having ordinary skill in the art would likely recognize still other types of means which may be provided for urging the end 48 of the stem 32 towards the end 20 of the valve body 12 while remaining totally within the scope of the present invention.

As shown, the valve body 12 has stem-engaging structure 86 near the first end 20 thereof for engaging with the head portion 34 of the stem 32 when the end 48 of the stem 32 is urged towards the first end 20 of the valve body 12 when the tip 62 of the instrument 22 is not engaged therewith, as shown in FIGS. 2A and 2B. Likewise, the stem 32 has valve body-engaging structure 88 near the end 48 thereof for engaging with the valve body 12 when the end 48 of the stem 32 is urged towards the first end 20 of the valve body 12. This engagement between the stem 32 and the valve body 12 provides that the aperture 58 on the end 48 of the head portion 34 of the stem 32 is urged closed when the end 48 of the stem 32 is urged towards the first end 20 of the valve body 12 and the tip 62 of an instrument 22 is not engaged therewith.

As shown, the stem-engaging structure 86 on the valve body 12 may comprise a taper 90 near the end 20 thereof. Preferably, the taper angle of the taper 90 is more than the taper angle of the conical surfaces 42 of the head portion of the stem 32. The valve body-engaging structure 88 on the stem 32 may comprise contact points 92 for engaging with the taper 90 at the end 20 of the valve body 12. When the end 48 of the stem 32 is urged towards the first end 20 of the valve body 12, as shown in FIGS. 2A and 2B, the taper 90 of the valve body 12 presses axially and radially against the contact points 92 on the head portion 34 of the stem 32 thereby urging the contact points 92 of the stem 32 towards each other. This urging causes the aperture 58 on the end 48 of the head portion 34 of the stem 32 to radially compress, and therefore close, with enough force to contain any internal pressure located in the fluid flow area 72. When the aperture 58 is fully closed, the compression spring 76 is extended to the position shown in FIGS. 2A and 2B, and the contact points 92 of the stem 32 project axially slightly past the extreme end of the end 20 of the valve body 12. This projection of the end 48 of the head portion 34 past the extreme end of the end 20 of the valve body 12 can be seen in FIGS. 1A, 1B, 2A and 2B, and provides that the end 48 of the head portion 34 of the stem 32 and adjacent areas can be cleaned. This feature is important in medical applications where bacteria growth on the end 48 of the head portion 34 and adjacent areas is to be avoided. To this end, a swab can be used to clean the end 48 of the head portion 34 of the stem 32 and adjacent protruding areas.

To further facilitate the closing of the aperture 58 when the tip 62 of an instrument 22 is not engaged therewith, the aperture 58 can be oval or oblong shaped as shown in FIGS. 3A and 3B. The aperture 58 shown is formed by the intersection of two offset circles. Specifically, preferably the aperture 58 has a minor axis aligned with the contact points 92 on the head portion 34 of the stem 32, and has a major axis aligned with the flats 46 on the head portion 34 of the stem 32, perpendicular to the contact points 92. As shown, the contact points 92 are adjacent the flats 46 on the head portion 34 of the stem 32. The diametral distance of the contact points 92 is greater than the diametral distance of the adjacent flats 46 (e.g., the diametral distance of the flats 46 is defined as the diameter of a circle just touching the flats 46 at the end 48). This enables the contact points 92 to receive most of the radial compression from the taper 90, closing the aperture 58 at its minor axis, or narrowest opening, in the direction indicated by arrows 94 in FIGS. 1A, 3A and 3B.

Operation of the valve 10 shown in FIGS. 1A, 1B and 2A–2C will now be described in connection with engagement of an instrument 22 therewith. As mentioned, the instrument 22 to be engaged with the valve 10 may be a needleless syringe having a cannula tip. Before the instrument 22 is engaged with the valve 10, the valve 10 looks as shown in FIGS. 1A, 1B and 2A. At that time, the end 48 of the stem 32 is sealed with the valve body 12, and the compression spring 76 or its equivalent structure effectively urges the end 48 of the stem 32 slightly out from the end 20 of the valve body 12. This urging by the compression spring 76 causes the taper 90 on the valve body 12 to press axially and radially against the contact points 92 on the head portion 34 of the stem 32, thus causing the aperture 58 on the end 48 of the head portion 34 of the stem 32 to radially compress. This compression is with enough force to cause the aperture 58 to close, thus containing any internal pressure within the fluid flow area 72. At this time, the stem 32 is hermetically sealed around the diameter which the contact points 92 on the stem 32 lie upon. At the opposite end 54 of the stem 32, a seal is created by constant compression of the stem 32 at the two sealing surfaces between the valve body 12 and the flat end portion 66 and adjacent lip 68 at the end 54 of the stem 32.

When the tip 62 of the instrument 22 is first brought to engagement with the aperture 58 in the end 48 of the stem 32, as shown in FIG. 2B, the aperture 58 resists the insertion thereof because of the force provided by the compression spring 76 on the stem 32. As the tip 62 of the instrument 22 is further pushed or engaged against the stem 32, the stem 32 is compressed and moved rearwardly against the action of the spring 76. At this time, it is preferred that there be very little, if any, contact between the valve body 12 and stem end 48. This movement causes the magnitude of the force due to the engagement of the contact points 92 on the stem 32 to lessen, and permits the tip 62 to enter into the aperture 58 and the instrument 22 is engaged with the end 20 of the valve body. The aperture 58 is free to expand to accommodate the tip 62 as shown in FIG. 2C, and creates a tight hermetic seal therearound. As shown in FIGS. 2A–2C, a female Luer lock thread 96 may be provided on the valve body 12 near the end 20 thereof for engagement with a corresponding male Luer lock thread 98 on the instrument 22. Or, other corresponding structure may be provided between the valve 10 and the instrument 22 for engagement therebetween. It is preferable to provide the described Luer lock threads or some other engagement structure because the engagement between the valve 10 and the instrument 22 helps to align the instrument 22 while providing a mechanical advantage to overcome the resistance by the aperture 58 to expanding and accommodating the tip 62 of the instrument 22. However, it should be pointed out that engagement between the valve body 12 and the instrument 22 is not necessary to keep the tip 62 of the instrument 22 and the aperture 58 of the stem 32 engaged because the grip or the frictional engagement of the aperture 58 around the tip 62 is sufficient to hold the instrument 22 and the valve 10 in engagement in most cases. Nevertheless, it may be desirable to provide the above-described Luer lock threads 98 and 96 on the instrument 22 and valve body 12, respectively, or some other engagement structure, when large separation forces will be present therebetween. This, of course, will depend on the application in which the valve 10 is used.

After the tip 62 of the instrument 22 is engaged with the aperture 58, fluid may be injected or withdrawn via the tip 62 through the stem 32, that is to say, the instrument 22 may suction fluid through the stem 32. Regardless, fluid can travel axially along the fluid flow area 72 formed by the fluid passageway 56 in the stem 32 and the reduced diameter section 18 of the valve body 12. As the fluid flows, no fluid enters the neutral space 74 between the stem 32 and the valve body 12. Therefore, bacteria growth in the neutral space 74 is not encouraged. Additionally, the compression spring 76, if provided, does not get exposed to the fluid passing through the valve. Therefore, there can be no leaching of harmful metals into the fluid stream.

As the tip 62 of the instrument 22 is withdrawn from the aperture 58 in the end 48 of the stem 32 (shown in the progression from FIG. 2C to FIG. 2B to FIG. 2A), the compression spring 76 forces the stem 32 towards the end 48 of the valve body 12 and against the taper 90. As a result of this constant bias of the stem 32 towards the tip 62, the aperture 58 in the stem 32 and adjacent internal stem walls wipe the tip 62 virtually free of fluid. This reduces waste of fluids. For example, in medical applications, this can reduce the waste of expensive injectable solutions and minimize human exposure to the fluid, which may be a biohazardous fluid.

After the tip 62 has been removed from the aperture 58, the valve 10 looks again as shown in FIG. 2A. At that time, the external surface of the end 48 of the stem 32, and the external surface of the end 20 of the valve body 12 can be wiped clean with a sterile swab, thus leaving no perceptible areas for bacteria growth. At this time, the valve 10 forms a positive seal as a result of the compression spring 76 (or other means such as a more robust stem throat section 36) urging the head portion 34 of the stem 32 against the taper 90 at the end 20 of the valve body 12. As a result of this positive seal, if pressure is exerted on the fluid line (not shown) connected to the end 24 of the valve 10, the valve 10 will not leak. In fact, this pressure will further force the stem 32 into the taper 90 thus enhancing or heightening the seal created at the aperture 58 at the end 48 of the stem 32.

The above-described valve 10 provides several advantages over the prior art. For example, the neutral space 74 is sealed away from the fluid flow through the valve 10. Therefore, there is no leaking of fluid thereinto, and the compression spring 76 (if provided) is not exposed to the flowing fluid. Also, the tip 62 of the instrument 22 is wiped virtually free of fluid upon the tip 62 being withdrawn from the valve 10. Additionally, the valve 10 provides no perceptible areas for bacterial growth. Many more advantages are provided by the present invention and have been previously described herein. Even more advantages may readily be realized by one having ordinary skill in the art.

While description of the present invention has been so far made with reference to FIGS. 1A, 1B and 2A–2C, many modifications to the specific structure shown is entirely possible and anticipated. Some of these modifications are shown in the other Figures, and will now be specifically addressed.

FIGS. 4A–4C show alternatives to the structure of the valve body 12 shown in FIGS. 1A, 1B and 2A–2C. Because there is much similarity therebetween, reference numerals of identical parts and discussion relating thereto will be omitted with the understanding that one may review FIGS. 1A, 1B and 2A–2C and the discussion relating thereto in order to obtain a workable understanding thereof.

FIG. 4A shows a valve 10a identical to the valve 10 shown in FIGS. 1A, 1B and 2A–2C, but includes a snap joint 32 between a female front portion 26a and a male rear portion 28a of the valve body 12a. Other than this difference, there is no difference between the valve 10a shown in FIG. 4A and the valve 10 shown in FIGS. 1A, 1B and 2A–2C.

FIG. 4B shows a valve 10b exactly like the valve 10 shown in FIGS. 1A, 1B and 2A–2C, except that the male rear portion 28b of the valve body 12b is shaped for a male slip Luer connection with a fluid line (not shown).

FIG. 4C shows a valve 10c exactly like the valve 10 shown in FIGS. 1A, 1B and 2A–2C, but the male rear portion 28c of a valve body 12c has a male Luer lock thread 100 thereon for engaging corresponding structure on a fluid line (not shown).

Each pair of FIGS. 5A and 5B, 6A and 6B, 7A and 7B, 8A and 8B, and 9A and 9B shows a different aperture which may be implemented on a stem identical to the stem 32 shown in FIGS. 1A, 1B, 2A–2C and 3A–3F, in connection with the present invention. Because the stems shown in FIGS. 5A and 5B, 6A and 6B, 7A and 7B, 8A and 8B, and 9A and 9B are otherwise identical to the stem 32 shown in FIGS. 1A, 1B, 2A–2C and 3A–3F, reference numerals of identical parts and discussion relating thereto are omitted with the understanding that one may review FIGS. 1A, 1B and 2A–2C and the discussion relating thereto in order to obtain a workable understanding thereof.

Specifically, FIGS. 5A and 5B show an aperture 58a on a stem 32a where the first half 102a of the aperture 58a has a ramp 104 thereon for engaging a peaked flange 106 on the other half 108a of the aperture 58a when the aperture 58a closes in accordance with the present invention. FIGS. 6A and 6B show an aperture 58b on a stem 32b where the first half 102b of the aperture 58b has a squared slot 110 thereon for engaging with a key 112 on the other half 108b of the aperture 58b when the aperture 58b closes in accordance with the present invention. FIGS. 7A and 7B shows a stem 32c having a flap 114 within the stem 32c for covering the aperture 58c when the two halves 102c and 108c are forced together in accordance with the present invention.

FIGS. 8A and 8B show an aperture 58d on a stem 32d where the first half 102d of the aperture 58d has a curved slot 116 thereon for engaging with a key 118 on the other half 108d of the aperture 58d when the aperture 58d closes in accordance with the present invention. Finally, FIGS. 9A and 9B show an aperture 58e on a stem 32e where the first half 102e of the aperture 58e has a peaked valley 120 thereon for engaging a peaked flange 122 on the other half 108e of the aperture 58e when the aperture 58e closes in accordance with the present invention. Of course, still other apertures may be used in accordance with the present invention.

While embodiments of the present invention are shown and described, it is envisioned that those skilled in the art may devise various modifications of the present invention without departing from the spirit and scope of the appended claims.

What is claimed is:

1. A valve engageable with an instrument, said valve comprising: a valve body; a deformable stem located in said valve body and shiftable from a first position, said stem having a first end and a second end opposite said first end, said stem having an aperture at said first end, said aperture configured such that when the instrument is engaged with said aperture in said stem, said stem is urged from the first position and said aperture deforms to allow liquid to flow therethrough to or from the instrument, said stem including a conical portion generally proximate said first end, said conical portion converging along a longitudinal axis of said stem toward said first end of said stem, said stem and said valve body configured such that when the instrument is not engaged with said stem and said stem is in said first position, said valve body engages said conical portion of said stem, wherein the engagement between said valve body and said conical portion of said stem retains said stem in said valve body and urges said aperture closed.

2. A valve as recited in claim 1, wherein said valve body includes a shoulder and an internal wall adjacent said shoulder, said stem including a throat portion having an end portion which sealably contacts said shoulder and said internal wall of said valve body thereby providing two sealing surfaces between said throat portion and said valve body, said engagement between said throat portion and said valve body providing generally axial compressive resistance when the instrument is engaged with said aperture in said stem.

3. A valve as recited in claim 2, wherein the stem and valve body are configured such that the end of the throat portion of the stem sealably contacts said shoulder and said internal wall of said valve body when said stem is in the first position.

4. A valve as recited in claim 1, said valve body having stem-engaging structure on an internal surface thereof for engaging said stem when said stem is urged into said first position, said stem having valve-body engaging structure for engaging said stem-engaging structure on said valve body.

5. A valve as recited in claim 4, said stem-engaging structure on said valve body comprising a taper, said valve-body engaging structure on said stem comprising at least one contact point which engages said taper when said stem is urged into said first position.

6. A valve as recited in claim 5, a taper angle of said taper of said valve body being greater than a taper angle of said conical portion of said stem.

7. A valve as recited in claim 1, said stem configured such that said first end of said stem protrudes past an end of said valve body, thereby exposing said first end of said stem when said stem is in said first position.

8. A valve as recited in claim 7, wherein said aperture is generally oblong-shaped.

9. A valve as recited in claim 1, further comprising a compression spring between said valve body and said stem and in contact with said valve body and said stem, said compression spring urging said stem into said first position.

10. A valve as recited in claim 1, wherein the engagement between the conical portion of the stem and the valve body provides that no other engagement is needed between the stem and the valve body to retain the stem generally in the valve body when the stem is in the first position.

11. A valve as recited in claim 1, wherein when the stem is in the first position, the conical portion of the stem contacts the valve body and the second end of the stem contacts the valve body and no other part of the stem contacts the valve body.

12. A valve engageable with an instrument, said valve comprising: a valve body; a deformable stem located in said valve body and shiftable from a first position, said stem having a first end and a second end opposite said first end, said stem having an aperture at said first end, said aperture configured such that when the instrument is engaged with said aperture in said stem, said stem is urged from the first position and said aperture deforms to allow liquid to flow therethrough to or from the instrument, structure between said valve body and said stem and in contact with said valve body and said stem, said structure urging said stem into said first position, said stem including a conical portion generally proximate said first end, said conical portion converging along a longitudinal axis of said stem toward said first end of said stem, said stem and said valve body configured such that when the instrument is not engaged with said stem and said stem is urged into said first position, said valve body engages said conical portion of said stem, wherein the engagement between said valve body and said conical portion of said stem retains said stem in said valve body and urges said aperture closed.

13. A valve as recited in claim 12, wherein said valve body includes a shoulder and an internal wall adjacent said shoulder, said stem including a throat portion having an end portion which sealably contacts said shoulder and said internal wall of said valve body thereby providing two sealing surfaces between said throat portion and said valve body, said engagement between said throat portion and said valve body providing generally axial compressive resistance when the instrument is engaged with said aperture in said stem and said stem is urged from said first position.

14. A valve as recited in claim 13, wherein the stem and valve body are configured such that the end of the throat portion of the stem sealably contacts said shoulder and said internal wall of said valve body when said stem is in the first position.

15. A valve as recited in claim 12, said valve body having stem-engaging structure on an internal surface thereof for engaging said stem when said stem is urged into said first position, said stem having valve-body engaging structure for engaging said stem-engaging structure on said valve body.

16. A valve as recited in claim 15, said stem-engaging structure on said valve body comprising a taper, said valve-body engaging structure on said stem comprising at least one contact point which engages said taper when said stem is urged into said first position.

17. A valve as recited in claim 16, a taper angle of said taper of said valve body being greater than a taper angle of said conical portion of said stem.

18. A valve as recited in claim 12, said stem configured such that said first end of said stem protrudes past an end of said valve body, thereby exposing said first end of said stem when said stem is in said first position.

19. A valve as recited in claim 12, wherein said aperture is generally oblong-shaped.

20. A valve as recited in claim 12, wherein said structure between said valve body and said stem which is in contact with said valve body and said stem and urges said stem into said first position comprises a compression spring.

21. A valve as recited in claim 12, wherein the engagement between the conical portion of the stem and the valve body provides that no other engagement is needed between the stem and the valve body to retain the stem generally in the valve body when the stem is in the first position.

22. A valve as recited in claim 12, wherein when the stem is in the first position, the conical portion of the stem contacts the valve body and the second end of the stem contacts the valve body and no other part of the stem contacts the valve body.

* * * * *